United States Patent [19]

Chapolini

[11] Patent Number: 5,014,715
[45] Date of Patent: May 14, 1991

[54] DEVICE FOR MEASURING THE IMPEDANCE TO FLOW OF A NATURAL OR PROSTHETIC VESSEL IN A LIVING BODY

[76] Inventor: Robert J. Chapolini, 9907 Forge Park Rd., Perry Hall, Md. 21128

[21] Appl. No.: 275,224

[22] Filed: Nov. 22, 1988

[51] Int. Cl.$^5$ .............................................. A61B 5/02
[52] U.S. Cl. ................................. 128/672; 128/691; 128/713; 604/67
[58] Field of Search ............................... 128/672–675, 128/691–694, 713, 734; 604/50, 65–67

[56] References Cited

U.S. PATENT DOCUMENTS

| | | | |
|---|---|---|---|
| 3,847,138 | 11/1974 | Gollub | 604/50 X |
| 3,871,361 | 3/1975 | Kamen | 128/672 |
| 4,080,966 | 3/1978 | McNally et al. | 128/673 X |
| 4,392,849 | 7/1983 | Petre et al. | 604/50 X |
| 4,718,891 | 1/1988 | Lipps | 604/66 X |
| 4,798,211 | 1/1989 | Goor et al. | 128/673 X |

Primary Examiner—Kyle L. Howell
Assistant Examiner—J. P. Laeyk
Attorney, Agent, or Firm—Howard W. Califano

[57] ABSTRACT

A highly automated device to measure the impedance to fluid flow of a vessel by means of direct injection at normal physiologic pressures. The device produces objective impedance data including dynamic impedance, capacitance, and Direct Current resistance, without operator induced error. The device can be used for intraoperative impedance measurements by directly cannulating the vessel under study. Non-operative impedance measurement is performed by means of percutaneous catheters. The device can also inject imaging materials or a lytic solution into the vessel while also measuring vessel impedance.

23 Claims, 8 Drawing Sheets

DEVICE FOR MEASURING THE IMPEDANCE TO FLOW OF A NATURAL OR PROSTHETIC VESSEL IN A LIVING BODY

BACKGROUND OF THE INVENTION

1. Field of the Invention

The invention relates to a device for measuring the impedance to fluid flow of a vessel in a living body. The term "vessel," as used herein, refers, but is not limited to blood vessels, biliary tract vessels, urinary tract vessels, lymphatic channels, and various natural and prosthetic conduits that are used to replace or bypass these vessels. In specific, the device produces impedance measurements of the vessel including "direct current resistance," "dynamic impedance" and "capacitance" (these terms will be defined later in this specification).

2. Description of Prior or Contemporary Art

In the practice of clinical and research medicine, it is not infrequent that a practitioner needs to ascertain the impedance to the passage of fluid flow of a vessel structure. The impedance of a vessel can be markedly altered by various natural disease processes.

There have been many prior art devices utilized to determine only flow (not impedance) through blood vessels. Various sensors such as Doppler ultrasound, electromagnetic flow probes, and fiber optic catheters can measure flow. A limiting feature of these methods is the need for pre-existing flow in the vessel, which may not always be present. For example, a proximal obstruction in a blood vessel under study could reduce the distal flow velocity to the point that it is not measurable by these prior art devices. It is this distal vasculature that the physician is most interested in.

Very low flow systems such as the biliary tract cannot have their flow velocities determined by these current methods. The practitioner has to resort to using imaging methods which provide no direct impedance data, and are subject to interpretation. Only the method of impedance determination by direct injection can give objective, reproducible data in all of these cases.

The following published papers by clinical investigators report the use of direct injection to measure DC impedance: Ascer E., Veith F., Morin L.: "Components of Outflow Resistance and their Correlation with Graft Patency in Lower Extremity Arterial Reconstructions," J. Vasc. Surgery, 1:817-28, 1984; and, Parvin S., Evans D., Bell, P.: "Peripheral Resistance Measurement in the Assessment of Severe Peripheral Vascular Disease," Br. J. Surgery, 72: 751-3, 1985. U.S. Pat. No. 4,585,010 issued to Ascer et al., also teaches a manual injection technique of measuring vascular impedance.

In all cases indicated above, the investigators have used either hand injection techniques or mechanical injection by constant flow pumps. In the cases of hand injection techniques, a pressure wave form is generated. By integrating this curve, an average resistance value can be calculated. This method assumes that vessel resistance is a constant—this is an over simplification of the way blood vessels behave. The relationship of pressure and flow is not a linear function. Investigators who have used mechanical constant flow pumps have measured the pressure that is developed at a particular flow setting to calculate DC resistance. The problem of using a constant flow pump is that the resulting vessel pressure may be well outside of the physiologic pressure that this vessel is subject to. The resistance data could actually mislead the clinician. Furthermore, using resistance data obtained in this fashion may not be a valid method of comparing the severity of vessel disease to other patients, since the pressures at which the resistance values are determined are not necessarily within the same range for each patient. Another major problem with this method is the possibility of over pressurizing the vessel during testing and causing possible damage to it.

Capacitance measurements by direct injection and dynamic impedance measurements have not been reported in the medical or patent literature.

SUMMARY OF THE INVENTION

The present invention provides a means for accurately and reproducibly measuring flow impedance in a vessel by means of direct injection. The invention can be used for intraoperative impedance measurements by directly cannulating the vessel under study, or for non-operative impedance measurements by means of a percutaneous catheter.

The impedance of a vessel structure characterizes its ability to conduct fluid, either in a pulsatile or non-pulsatile flow pattern. The determinants of vessel impedance include the physical dimensions of the vessel itself and the makeup of its walls, and disease processes that may alter these two. This concept of impedance can best be discussed with reference to an electrical analogy, where: (1) impedance to steady state fluid flow is analogous to direct current (DC) resistance; (2) the stretchability of the vessel is analogous to electrical capacitance; and, (3) the response of the vessel to a pulsatile flow of fluid is analogous to dynamic impedance (reactance).

Impedance to steady state flow (i.e., DC resistance) refers to the relationship of a non-pulsatile fluid flow and the resulting vessel pressure, which is given by the following equation:

$$DC\ Resistance = \frac{P}{Q} \text{ where } \begin{array}{l} P = \text{pressure} \\ Q = \text{Flow} \end{array}$$

In most anatomic vessel structures, the relationship of nonpulsatile flow and pressure is not linear. It is, therefore, important that the DC resistance be determined over the range of physiologic pressures normally present in the vessel under study. In the present invention, the DC impedance is measured by a device comprising: an automated injection means for injecting fluid into the vessel; a pressure sensor means for measuring the luminal pressure of the vessel; a feedback control means, operably coupled to said automated injection means and said pressure sensor means, for automatically adjusting the fluid flow rate so as to maintain luminal pressure at a preset value; and, a means, operably connected to the automated injection device so that the flow rate may be measured at the maintained, preset luminal pressure. Generally the flow rate needed to generate a luminal pressure is determined for each of a plurality of preset pressure values, thereby allowing for the construction of a pressure-resistance curve for the vessel.

The stretchability of the vessel, or capacitance, is defined by the following equation:

$$capacitance = \frac{D\ Volume}{D\ Pressure}$$

A fluid conducting vessel can be thought of as a Resistance-Capacitance network. The vessel can be charged to a specified pressure, and a pressure decay curve can then be determined for that vessel. The time constant of pressure decay ($\tau$) is then determined from the slope of the pressure decay curve. The following equation relates the time constant and resistance to solve for the capacitance of the vessel:

$$\text{Capacitance} \frac{\tau}{\text{Resistance}}$$

The capacitance of a fluid vessel can provide much information on disease processes. It can also be important for impedance matching of conduits, both autologous and prosthetic, used to replace or bypass obstructions in these vessels. The present invention accomplishes capacitance measurements by charging the vessel to a selected lumen pressure followed by an immediate cessation of injection flow. The luminal pressure is monitored immediately after cessation of injection for a preset time period, thus producing a pressure time decay curve for the vessel.

The response of the vessel to a pulsatile flow of fluid (dynamic impedance), is also determinable by the present invention. As in the electrical analogy, dynamic impedance is a frequency dependant impedance. By applying a known pulsatile fluid flow in a vessel, one can obtain valuable dynamic impedance information about the vessel, including longitudinal and transverse impedance, both of which are frequency dependent. The present invention uses the following basic elements to measure dynamic impedance: an automated injection means for injecting fluid in a pulsatile manner; a control means for controlling the injection means to inject a pulsatile flow generally matching a target fluid pressure-time profile, a means operably connected to the automated injection means for monitoring the instantaneous flow rate of injection; and, a pressure sensor means for measuring the luminal pressure of the vessel during and between each pulsatile injection. The control means can measure luminal pressure and successively alter the injected pulse profile until the measured pressure-time profile matches the target pressure-time profile. The vessel's pressure-time profile can then be compared to the flow-time curve.

The present invention would have application not only in measuring the impedance of blood vessels or bypass vessels, but can also be used to measure flow impedance in biliary or urinary track vessels, thereby detecting intraluminal obstructions, extraluminal compression (such as by a tumor pressing on the vessel), and disease processes effecting the walls of these vessels. The invention also can be used to inject contrast material to image these vessels, or lytic solutions to dissolve obstructions in these vessels, in a controlled, safe manner.

A first novel feature is the use of an automatic injection means operated by a control computer to accurately and reproducibly measure the impedance to flow of a fluid conducting vessel by direct and controlled fluid injection into the study vessel. The injection pressures used are controlled by the device itself, and are typically over the physiologic range that the study vessel normally encounters. The injection pressures are generally measured in the lumen of the study vessel so that accuracy is ensured.

A second novel feature is the use of the automatic injection means to produce a constant preselected luminal pressure in the study vessel. The rate of injection is automatically measured and information is collected so that DC resistance of the vessel can be calculated.

A third feature is the use of a control computer to automatically control the injection means so that the DC resistance of a vessel for a plurality of preselected luminal pressures can be determined. The control computer will automatically sequence the injection means from one pressure to the next, while the flow rate for each pressure is established. A resistance v. pressure curve is generated.

A fourth feature is an automatic injection means sequenced by the control computer so that capacitance of the vessel can be determined. The injection means will produce a predetermined pressure in the study vessel, and then stop. The pressure decay over time is then passively measured This information along with resistance data, will allow the invention to calculate the capacitance of the study vessel A fifth novel feature is the use of the automatic injection means to apply a pulsatile fluid pressure to the study vessel while the flow of the injected fluid is monitored. The collected data are used to calculate the frequency dependent impedance to flow—that is the dynamic impedance.

A sixth novel feature is to use the automatic injection means to apply a pulsatile fluid pressure to an obstructed vessel, distal to the obstruction, that has a pressure-time profile similar to that measured proximal to the obstruction. The control computer uses successive approximation to achieve the proximal driving pressure curve. This feature enables one to predict the flow that will result if the obstruction is removed or bypassed.

A seventh novel feature of the present invention is to use the predicted flow rates, in order to calculate the flow velocities of bypass grafts of various sizes and compliances, in order that the best suited bypass graft is chosen for the procedure.

An eighth novel feature is to use the automatic injection means controlled by the computer means to inject dyes and contrast materials at a controlled vessel luminal pressure. This allows one to safely image these vessels either optically, radiographically or by other scanning methods that require such contrast materials. This differs from currently used techniques, which do not use constant vessel luminal pressure monitoring as a limiting factor for injection rates.

A ninth feature is a cannula means used with the present invention for measuring the percentage of the total impedance to flow that is present in each limb of a vessel with a bidirectional flow. An example of this situation is seen in the case of a bypass conduit being connected to the side of a recipient vessel, such that the resultant flow from the conduit into the recipient vessel could be both retrograde as well as antegrade.

A tenth novel feature is a cannula means used with the present invention for measuring vessel impedance during operative procedures. The cannulating device is designed to provide for atraumatic insertion through an incision made directly in the vessel under study, or through the transected end of said vessel. The cannulating device provides for a water tight seal between itself and the vessel. The cannulating device provides for direct monitoring of the luminal pressure of the study vessel during and between injection cycles.

An eleventh novel feature is a percutaneous catheter used in association with the automatic injection means to provide a means for non-operatively measuring vessel impedance. The catheter contains both injection and pressure monitoring lumens and a means for providing a water tight seal between itself and the inside vessel wall, proximal to the injection and monitoring ports.

A twelfth novel feature is the use of the injection means controlled by the control computer to calculate intraluminal vessel pressure and use the data to control the injection rate of a thrombolytic agent. The injection rate is constantly measured and impedance calculated so that the effectiveness of the thrombolytic therapy can be evaluated.

The above-mentioned features, as well as other features and advantages of the present invention, all become readily apparent from the following non-limiting description and the accompanying drawings.

SUMMARY OF THE DRAWINGS

The above-enumerated objects and features of the present invention will more fully appear from the following detailed description when read in conjunction with the accompanying drawings. It is to be understood that the drawings are for the purpose of illustration only and are not intended as a definition of the limits of the invention.

BRIEF DESCRIPTION OF PREFERRED EMBODIMENTS

Figure 1:
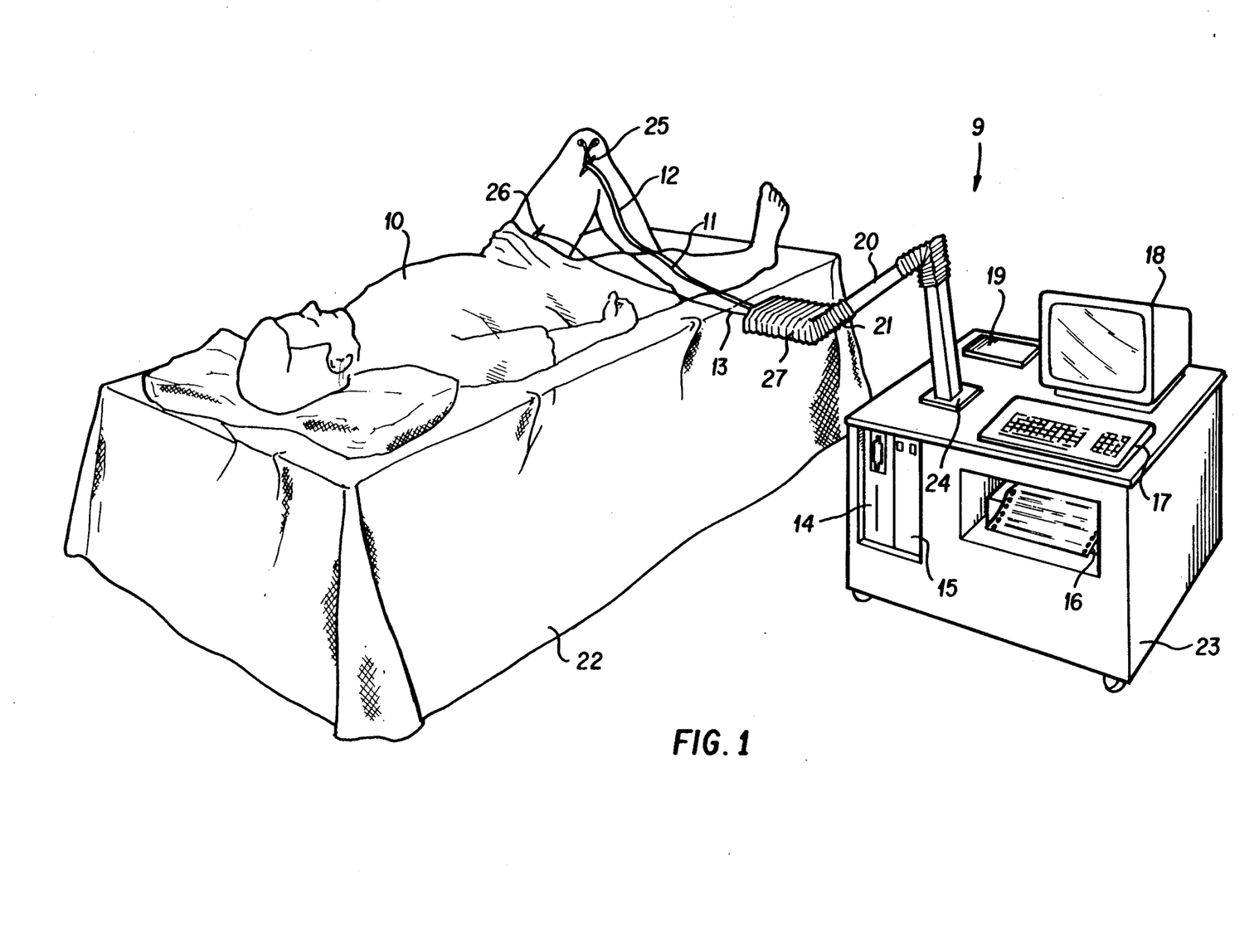
FIG. 1 is a view of the vessel impedance analyzer, as taught by the present invention, being used in an operating room during a vascular bypass procedure.

In FIG. 1, preferred embodiment of the invention is shown being used during a vascular bypass operation. The injection module 27 is suspended over the operative field with the injection tubing 11, 12 connecting the injection module 27 to the blood vessel to be analyzed 25. A smaller pressure monitoring tubing 13 is shown leading from the injection module 27 to the incision at the site of the donor blood vessel 26 (the source of blood flow for the bypass procedure) and inserted into the donor vessel for the purpose of measuring the driving force that will be exerted on the recipient blood vessel.

The injection module 27 is suspended over the patient 10 by an articulated boom 20 so that the connection length between the injection module 27 and the vessels under study 25, 26 may be minimized. A sterile sleeve 21 fits slidably over the injection module 27 and up the articulated boom 20 in order to maintain sterile integrity during use of the device.

A mobile table unit 23 provides for support of the articulated boom 20 and for containment of the various subcomponents. A video monitor 18 displays all data for immediate inspection by the operator, located at the operating table 22. An auxiliary keyboard 17 is provided on the mobile base 23 for operation of the analyzer by personnel not directly taking part in the operative procedure.

Control of the testing sequence, processing of data, and mass storage of data are accomplished by the control computer 14. A variety of control software is utilized by the control computer 14 for the testing of different impedance parameters.

A dedicated printer 16, is shown located in the mobile base unit 23. It provides for a permanent record of the test results for the physician and patient's records. A communications module 19 provides for collection of patient data at a centralized collection location and also provides for a means of transmitting the impedance data for analysis by medical personnel remote to the surgical procedure.

An interface module 15 provides for a connection of the control computer 14 and the injection unit 27 and its various electronic components.

Although the preferred embodiment of the invention is shown in FIG. 1, it should be understood that alternate configurations of the components may be utilized. Alternate embodiments of the invention include a completely integrated, portable unit that, as a single unit, may or may not be included in the sterile operative field. Other embodiments of the invention include one with a detachable injection module that may be placed directly on the sterile field, its connections to the control computer via a hard wire connection or various means of wireless data transmission.

Figure 2:
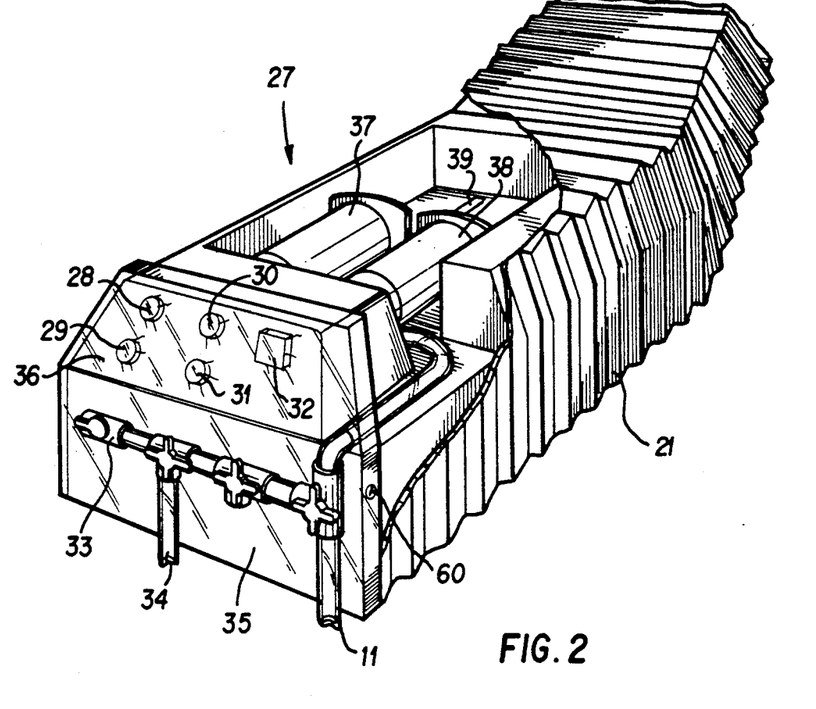
FIG. 2 is an enlarged view of the injection module of the impedance analyzer showing a twin syringe injection system and the protective sterile sleeve in place.

As shown in FIG. 2, the injection unit may include one or more syringe pumps 37, 38 which are mounted in an elongated enclosure 27. The injection pump may contain a primary 37 and a secondary 38 syringe pump, although it should be understood that only one syringe pump or more than two syringe pumps may be used in other embodiments.

Connected to the injection end of the primary 37 and secondary 38 syringes is the main injection tubing 11. This connection tubing 11 pierces the front cover plate 35 and passes through a three way valve 63 and to the test vessel 25. A connection from valve 63 and valve 64 allows for the remote filling of syringes 37, 38 and for the purging of air from the system. Valve 65 connects the remote pressure monitoring tubing 34 to the disposable pressure transducer 33, shown without its electrical connections. Injection pressure monitoring from the proximal main injection tubing 11 at the point of valve 63 is accomplished by appropriately configuring all control valves 63, 64, 65.

The primary and secondary syringes 37, 38, the main connection tubing 11, the control valves 63, 64, 65, the pressure transducer 33, the clear face plate 35, and the sterile sleeve 21, constitute a single use, disposable package intended to prevent contamination to the patient. It should be clear that alternate configurations of the tubing and valves may be utilized to allow for constant vessel lumen pressure monitoring during the impedance measurements.

Control of the test sequence is by single function keys 28, 29, 30, 31, 32 located on the front panel of the injection module 27. Sterile access to the function keys is through a flexible portion of the front cover plate 35.

The sterile sleeve 21 is shown in its unfurled state (FIG. 2.) A permanent bond connects the front cover plate 35 to the sterile sleeve 21. When the sterile sleeve is slid up the articulated boom 20 (FIG. 1) it along with the front cover plate 35, form a complete sterile barrier for the injection module.

Figure 3:
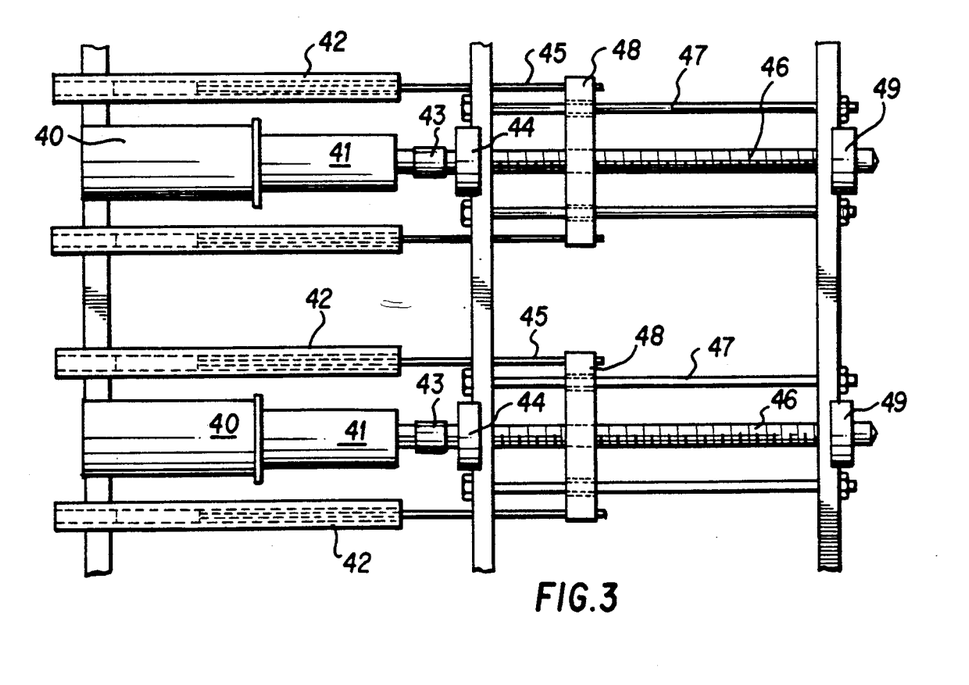
FIG. 3 is a view of the syringe drive mechanisms, position and velocity transducers shown being attached to the sliding drive block—twin injection system illustrated.

FIG. 3 shows the details of the dual syringe pump embodiment of the invention. The permanent magnet DC electric motor 40 is connected to the gear reduction box 41 whose output shaft is connected to the main screw drive shaft 46 by a coupling 43. Bearings 44, 49 provide for support of the main drive shaft 46. A mobile tapped block 48 translates the rotational movement of the main drive shaft 46 into linear motion. The linear mobile block 48 travels slidably along the guide rods 47.

Linear displacement transducers 42 provide for position data of the linear mobile block 48 and in turn, the position of the syringe piston 50. Real time velocity data of the linear mobile blocks 48 and the syringe pistons 50 are provided by the linear velocity transducers 66.

Figure 4:
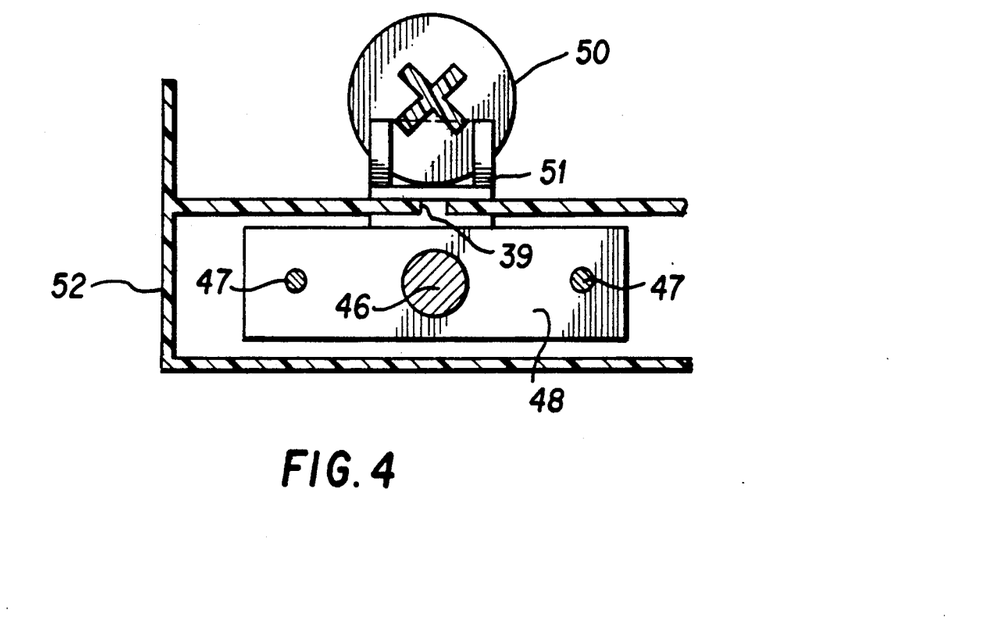
FIG. 4 is a front sectional view of the injection module showing the syringe piston being releasably attached to the sliding drive block.
Figure 5:
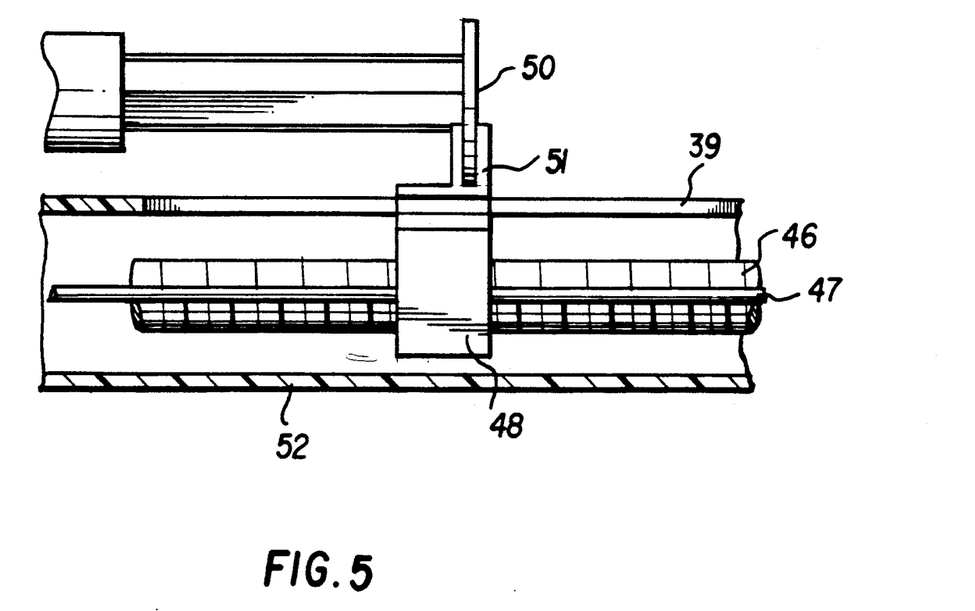
FIG. 5 is a side sectional view showing the syringe piston being releasably attached to the sliding drive block.

The linear mobile block 48 (FIG. 4) has its motion transmitted to the syringe piston 50 by an extension member 51 which travels through a slot 39 that is present in the injection unit case 52. The syringe piston end 50 is releasably connected to the extension member 51.

The design of the syringe pumps allows for the production of a large range of flow rates by using either one pump alone for low rates, or by using multiple syringe pumps simultaneously for higher flow rates.

The use of multiple syringe pumps also allows for a more accurate production of a pulsatile wave form. The primary pump could be used for generating a background pressure (e.g., the diastolic portion of an arterial wave form) and the secondary pump used for generation of the pressure peaks (e.g., the systolic portion of an arterial wave form).

In many naturally occurring situations, reversal of the direction of flow may take place during a pulsatile pressure cycle. To reproduce the pressure cycle, the individual syringe drives could be commanded to operate in different directions and at different speeds. The summation of the positive and negative flow rates would indicate the presence and the amount of reverse flow during the pulse cycle.

Although the preferred embodiment of the invention contains multiple syringe pumps, it should be understood that many of the functions of the invention could be accomplished with only a single syringe pump or any other positive displacement pumping system.

It should also be understood that alternate drive systems for the syringe pumps can be used including, but not limited to, hydraulic and pneumatic mechanisms.

In order to allow injection into a vessel and thereby measure its impedance to flow, several termini to the invention are utilized, depending on the type of vessel and whether the measurements are being conducted as part of a surgical procedure, or as a separate diagnostic procedure that is done percutaneously.

Figure 6:
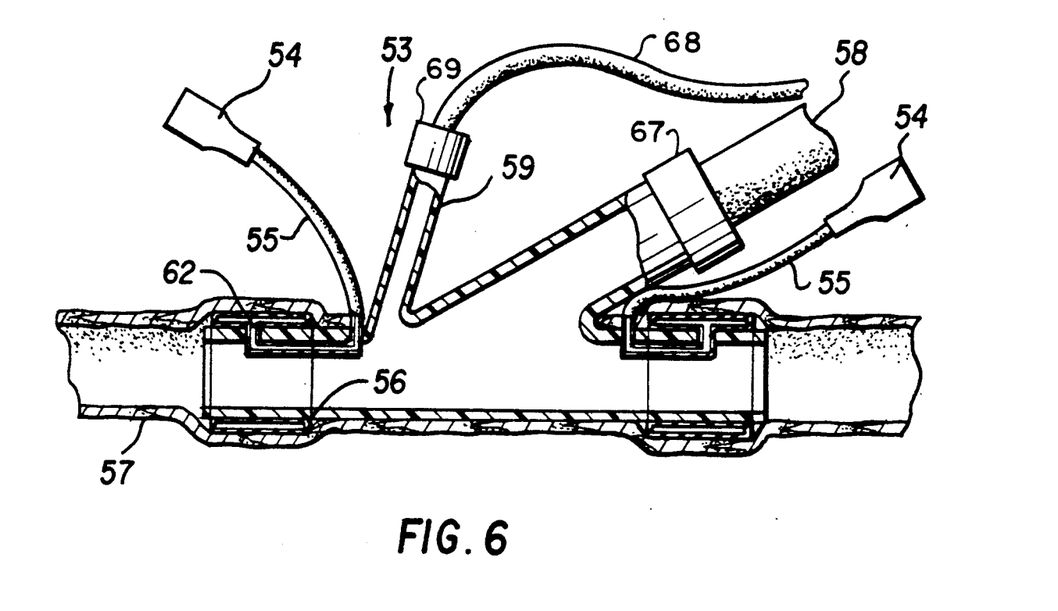
FIG. 6 is a view of a balloon sealing, bidirectional cannula for cannulating vessels intraoperatively.

For impedance measurements in a vessel with bi-directional flow taken during a surgical operation, the terminus illustrated in FIG. 6 is utilized. The vessel 57 has been exposed and opened longitudinally. The cannula 53 is inserted into the vessel 57, its size being approximately the size of the vessel lumen. Water tight seals between the cannula 53 and the vessel 57 are established by the balloons 56. The balloons are filled by inserting a needle connected to a syringe (not shown) into the fill port 54. The fluid or gas used to fill the balloons 56 flows down the tubing 55 and into the fill inlet 62.

Bi-directional injection into the vessel is accomplished through the injection tubing 58 which is connected to the cannula by a releasable connection 67. Monitoring of the vessel lumen pressure is accomplished through the pressure port 59 which is connected to the pressure monitoring line 68 by a releasable fitting 69. The use of releasable connections 67, 69 allows for selection of the appropriately sized cannula 53 for the vessel under study.

Figure 7:
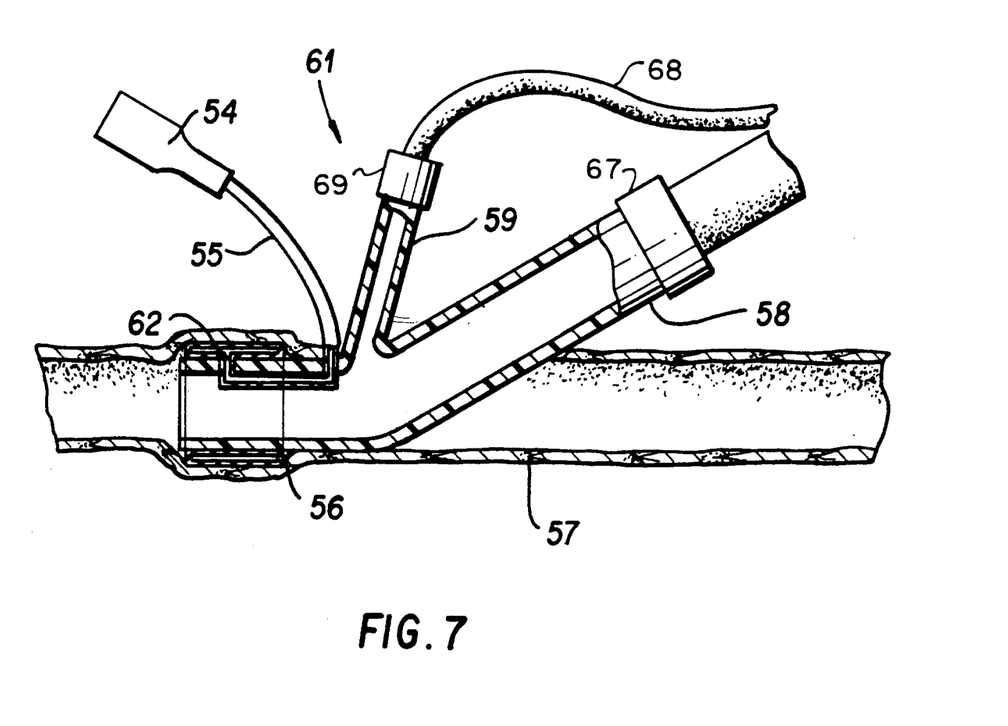
FIG. 7 is similar to the cannula in FIG. 6, except is used for unidirectional flow vessels or measuring individual components of multi-directional flow vessels.

FIG. 7 illustrates a cannula suitable for use in vessels with unidirectional flow, or for isolating the flow components of a vessel with multidirectional flow. The cannula is sealed to the vessel 57 by the use of the inflatable balloon seal 62.

Figure 8:
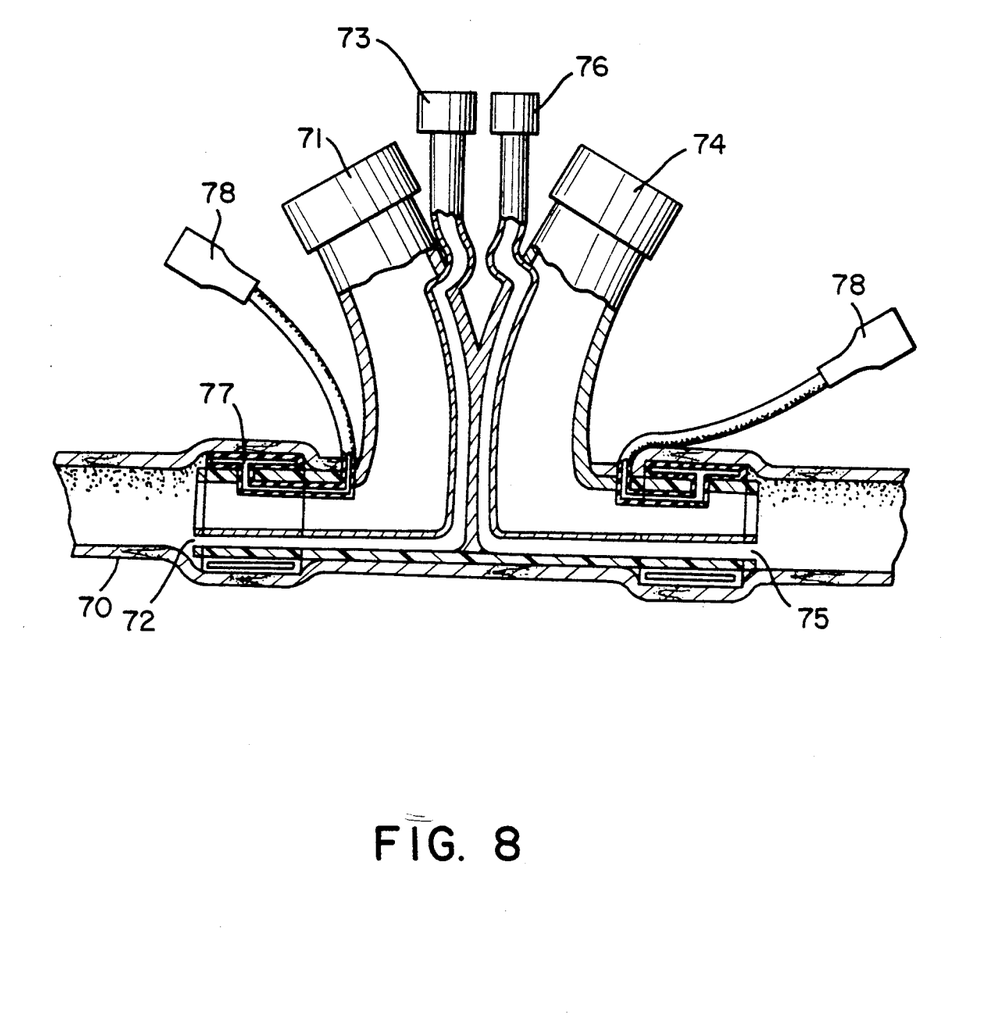
FIG. 8 is a side sectional view of a cannula that can provide independent impedance determination for each limb of a vessel with bidirectional flow characteristics.

FIG. 8 illustrates a cannula that can provide for independent impedance determination of each limb of a vessel with bidirectional flow characteristics. Downstream injection of the vessel 70 is through the injection line 71. Luminal pressure monitoring is through the pressure port 72 and is hydraulically transmitted to the transducer by the pressure monitoring line 73. A separate injection port 74 and pressure monitoring port 75 and pressure line 76 are provided for independent impedance determination of the upstream vessel. Balloon seals 77, which are filled by injecting fluid or a gas through the fill port 78, provide for the seal between the vessel 70 and the injection cannula.

Although these are the preferred embodiments of the terminus of the invention for use during operative procedures, it should be clear that alternate cannulas that provide for a water tight seal between themselves and the vessel to be studied may be utilized. These alternate cannulas would have a means of monitoring the luminal pressure of the vessel during the injection process and sending these data to the control unit.

Figure 9:
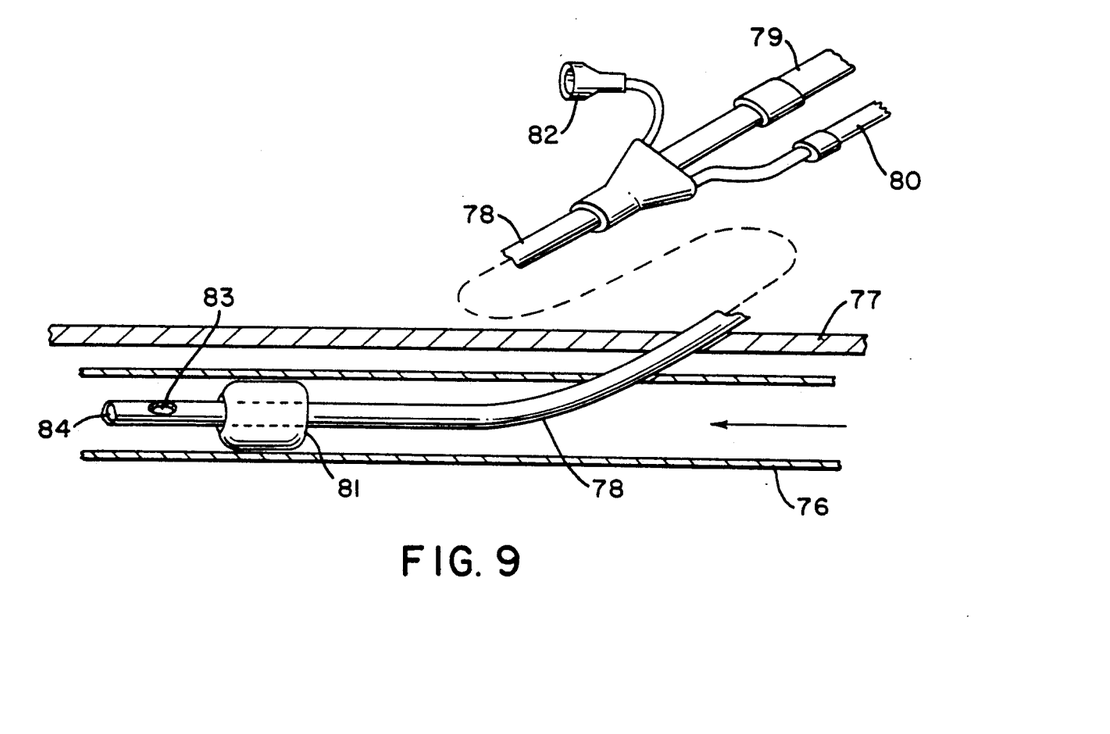
FIG. 9 is a cannula to be used for percutaneous vessel impedance measurements.

When used to measure the impedance to flow of a vessel by percutaneous methods, the preferred embodiment of the invention would have as its terminus, the cannula illustrated in FIG. 9. The vessel to be studied 76 is entered through the patient's skin 77 by using a needle, and by introducing a guidewire through the needle (not shown) and into the vessel. The cannula 78 is then introduced into the vessel 76 by passing it slidably over the guide wire.

Injection into the vessel by the invention is accomplished by the injection tubing 79 and through the terminal port of the cannula 84. Pressure monitoring of the vessel during injection is through the pressure port 83 which is connected to the pressure monitoring line 80. During the injection process, a water tight seal is maintained between the cannula 78 and the vessel 76 by means of a balloon seal 81, which is inflated by a gas or liquid containing syringe and needle (not shown) through the balloon fill port 82.

In cross section (FIG. 10), the balloon seal 81 is seen contacting the vessel 76 circumferentially. The multi-lumen design of the cannula is seen, with a separate balloon fill lumen 87, pressure monitoring lumen 86, and injection lumen 85. The pressure monitoring port 83, is located proximal to the injection port 84.

Although the preferred terminus for the invention to be used when vessel impedance is to be measured percutaneously is shown, alternate means of providing for the simultaneous injection into and pressure monitoring of a vessel lumen without surgical exposure of the vessel, may be utilized. This includes using methods of luminal pressure monitoring other than the hydraulic transmission of the pressure to a remote pressure transducer, such as seen in the present embodiment of the invention.

Furthermore, it should be clear that the terminus of the invention intended to be used percutaneously would also be useful for cannulation of vessels during a surgical procedure.

OPERATION OF THE DEVICE

For the intraoperative measurement of vessel impedance, the injection module 27 with its sterile cover plate 35, sterile sleeve 21, and associated syringes 37, 38 and valves 63, 64, 65 is positioned over the operative field in close proximity to the vessel to be studied. The appropriate type and size of cannula (FIGS. 6, 7, 8, 9) is chosen and inserted into a small incision made in the vessel. The cannula is connected to the injection tubing 11, which has been previously flushed free of air bubbles. The syringes 37, 38 are filled with the fluid to be used for the injection process (e.g., sterile electrolyte solutions or whole blood) through the fill valve 64. Control of the filling process is by the single function button 28.

The control computer needs to know the range of pressures normally experienced by the vessel segment to be studied. The computer generally follows the flow chart in FIG. 11 to establish the operating pressures. In the case of vascular surgery procedures, the patient's blood pressure waveform is measured and stored (90) in the control unit 14 by means of the pressure monitoring line 13 which is hydraulically connected to the pressure transducer 33. A needle or intravenous catheter (not shown) is attached to the end of the pressure monitoring line 13 and is inserted into the vessel, upstream of the obstructed vessel to be studied, or in the case of a vascular bypass procedure, into the donor vessel 26. The pressure wave form is then stored in the control unit 14 and its pressure over time is analyzed by the computer. Alternately, the patient's pressure wave form may be obtained from a remotely cannulated vessel, such as one used for routine blood pressure monitoring during an operation. The patient's blood pressure may also be manually entered (91) into the control unit 14 by using the auxiliary keyboard 17.

Figure 11:
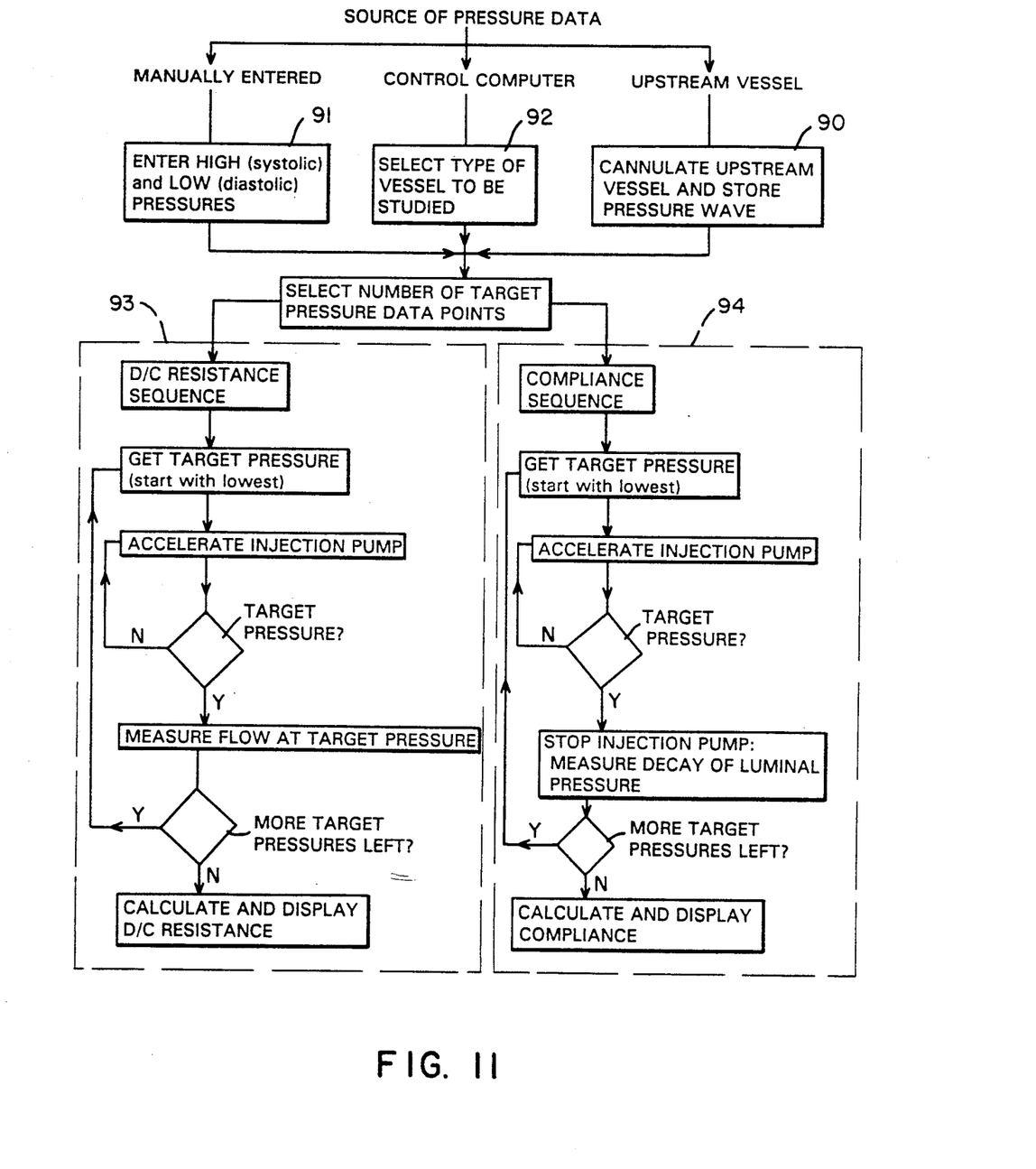
FIG. 11 is a flow chart of a software routine implemented in the control computer for DC impedance and capacitive impedance measurements.

In the case of impedance measurements in vessels that normally contain very low pressures (e.g., biliary vessels) the computer will suggest appropriate pressure limitations (92) to the operator.

After establishing the pressure operating limits (both a upper and lower limit) the invention is ready to measure the desired vessel impedance parameter (See subroutine 92, FIG. 11). In the case of DC resistance measurements, the primary injection syringe begins the injection process by accelerating its speed until the initial target luminal pressure is reached. Instantaneous vessel luminal pressure monitoring is by way of a hydraulic connection between the pressure transducer 33 and the cannula pressure monitoring port 59, 73, 76, or 80, using a connecting tubing 13, 34. This injection rate is maintained for a period of time to allow for pressure stabilization. After determining the flow rate at the first target injection pressure, the control computer directs the syringe pump to accelerate to the next target pressure. The process is continued until a number of flow-pressure data points are obtained for the study vessel. If the injection capacity of the primary syringe 37 is exceeded, the secondary syringe 38 automatically begins to augment the injection rate. The relationship between flow rates and luminal pressure, the DC resistance, can then be displayed immediately to the operator as a curve (resistance vs. pressure) or as an average numerical value. Individual pressure-flow data points may also be obtained by inputing single target pressure points into the control computer.

Vessel capacitance can be measured independent of DC resistance or in conjunction with it. Subroutine 94 in FIG. 11 generally shows the steps taken by the control computer to determine vascular capacitance. In order to measure capacitance independent of other impedance measurements, the vessel under study is cannulated by the appropriate terminus of the invention (FIGS. 6, 7, 8, 9). The operating pressure limits are entered into the control computer. After the injection tubing and syringes 11, 37, 38 are filled with either blood or sterile electrolyte solutions, the primary syringe 37 begins to accelerate to achieve a luminal pressure equal to the target pressure limit that has been established. When the target pressure is achieved, the flow rate is measured and a resistance for the vessel is established. The secondary syringe pump 38 will augment the flow rate if the capacity of the primary syringe pump 37 is exceeded. After the resistance information is obtained, the control computer 14 commands the syringe pumps to stop immediately. Electronic breaking is used to stop the syringe drive motors 40. The luminal pressure of the test vessel is then measured until the pressure drops to a minimum. This information is then used to produce a pressure decay curve for the test vessel. The slope of this curve is automatically determined by the control computer. The absolute value of the inverse of the slope of the decay curve produces a value called the time constant ($\tau$). A relationship between the time constant and the resistance of the resistance-capacitance network (i.e., the vessel segment under study) is then used to calculate the capacitance:

$$C = \frac{\tau}{\text{Resistance}}$$

The capacitance of a vessel can also be determined during the measurement of the DC resistance of the vessel. After determining the resistance at the highest pressure limit, the injection syringes 37, 38 are commanded to immediately stop. The pressure decay curve is then measured and the time constant is calculated. Thus, the capacitance is then calculated from the time constant and resistance data.

Capacitance calculations can be measured at several pressurization levels in order to obtain a capacitance vs pressure curve for the vessel segment.

Figure 12:
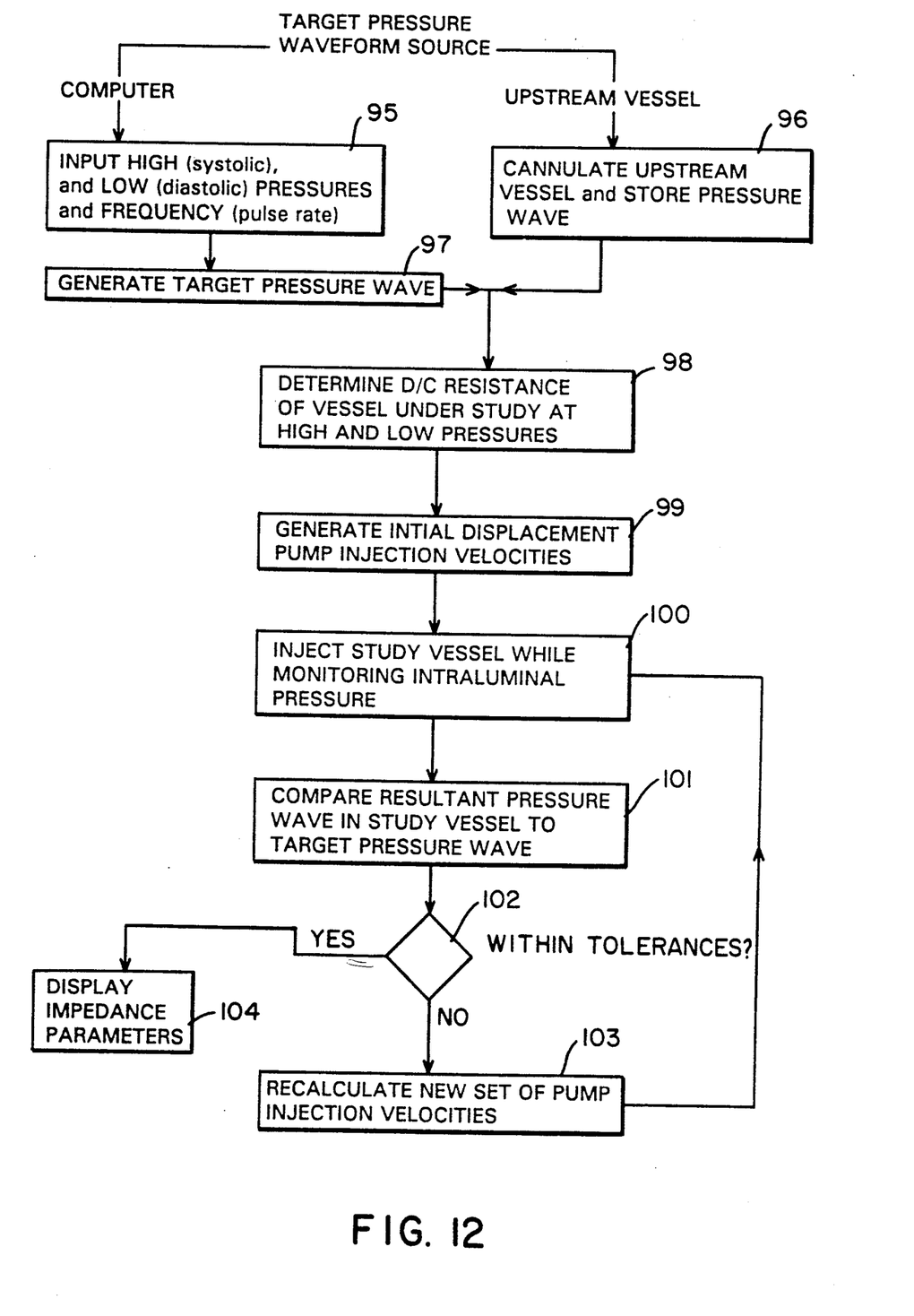
FIG. 12 is a flow chart for dynamic impedance measurement that is implemented in the control computer.

To measure the dynamic impedance of a vessel, a pulsatile flow is applied to the lumen while measuring the instantaneous flow rate. FIG. 12 is a flow chart of the technique as taught by the present invention, which is partly implemented in control computer 14. The vessel under study is cannulated by the appropriate cannula (FIGS. 6, 7, 8, 9) and the syringe pumps 37,38 and injection tubing 11, are filled with either sterile electrolyte solution or the patient's blood. The high and low pressure limits are then entered (95) into the control computer 14 (e.g., in the case of studying an artery, the patient's systolic and diastolic blood pressure are entered). The control computer 14 will then use these data along with the pulse frequency to generate a target pressure-time curve (97). Alternately, the patient's actual pressure curve may be entered (96) into the control computer 14 by inserting a small intravenous cannula (not shown) connected to the pressure monitoring line 13, 34 into a vessel that is receiving a normal pressure driving force (e.g., in the case of an obstructed arterial segment, the pressure waveform would be measured upstream to the obstruction). This target pressure waveform is thus stored in the control computer 14.

The approximate DC resistance of the test vessel is needed by the control computer in order to calculate the velocity profile to be used. If DC resistance has been previously determined for the vessel, these data are used for the calculations. If no DC resistance data are available for the vessel, the invention will determine DC resistance at the peak value of the pressure curve (systolic pressure) and at the lowest point of the pressure curve (diastolic pressure) (98). The first set of injection velocity profiles can then be calculated by control computer 14 from the resistance data (99).

The pulsatile driving force is applied to the test vessel, while monitoring the actual injection rate and instantaneous luminal pressure (100). After pulsing the vessel for one cycle, the control computer analyzes the resulting pressure-time curve that was generated. By comparing the actual pressure-time curve to the desired curve (101), adjustments to the injection velocity profile are made by the control computer (103). A second pulse is then applied to the vessel, and again the pressure-time curves are compared (101). By using this "successive approximation," a close match between the pressure-time curves can be attained. This "successive approximation" is accomplished by the control computer 14 implementing the software flow chart shown in FIG. 12.

When a close match is attained (102), several flow parameters can then be calculated (104): the flow at the point of maximum pressure during the cycle (maximum systolic flow); the point of maximum flow in the pressure cycle; the phase angle between the pressure and flow curves; the average flow per cycle; the presence of reverse flow during the cycle; instantaneous flow and pressure values at any point in the cycle.

If the actual pressure waveform of the vessel is entered into the control computer, upstream of a blockage, the amount of bloodflow that will exist in the vessel if the obstruction is removed or bypassed, can be determined before the procedure is completed. Successive approximation is used to produce a pressure-time curve in the vessel downstream of the obstruction that is equivalent to the upstream pressure-time curve. In the case of bypass surgery, this information can be used by the control computer to calculate the flow velocities that would exist in different diameter bypass conduits that are available, thereby allowing the operator to select the appropriate one. (The appropriate bypass conduit neither has too high of a flow, causing turbulence, nor too low a flow causing thrombosis). Furthermore, these data would allow for impedance matching of a bypass vessel to donor and/or recipient vessels.

As part of the investigation into the impedance to flow of a vessel, direct imaging of the vessel is often useful. The invention can be used to cannulate the study vessel and then automatically inject a contrast material (e.g., radiopaque contrast material, radioisotopes, dyes, etc.) automatically, at physiologic pressures that the vessel normally encounters. This is in contrast to currently used injection systems which do not control the rate of injection based on the developed pressure in the lumen of the study vessel. The risk of over-pressurizing the vessel is eliminated. The process is also automated, making it unnecessary for the operator to be in close proximity to radiation sources, as is often the case when x-ray imaging is done in operating rooms.

PERCUTANEOUS IMPEDANCE MEASUREMENTS

Figure 10:
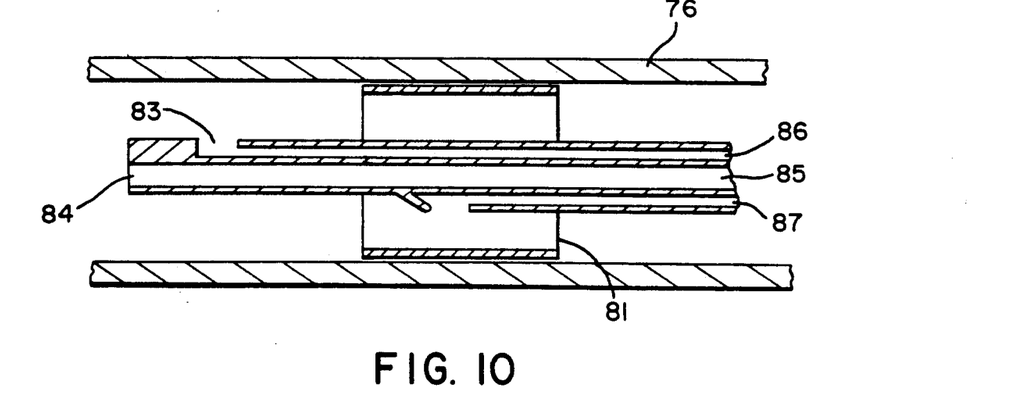
FIG. 10 is a longitudinal section of FIG. 8.

All of the aforementioned impedance analyses may be accomplished by using standard percutaneous methods of gaining non-operative access to the vessel to be studied. The cannulae shown in FIGS. 9 and 10 illustrate a preferred embodiment of such a device that will allow for percutaneous vessel impedance measurement. The vessel 76 is first entered by a needle, through which a guidewire is passed (not shown). The cannula 78 is then introduced into the vessel 76 by slidably passing it over the guide wire. The guide wire is then removed and the cannula is connected to the injection tubing 79. A separate pressure monitoring port 83 is connected to the pressure monitoring line 80.

The impedance parameters are measured in the same fashion as is done when the invention is used intraoperatively. The balloon 81, is used to effect a water tight seal between the cannula 78 and the test vessel 76. The amount of impedance that an obstruction to a vessel is causing is measured by placing the injection tip 84 just upstream of the blockage.

The amount of impedance to flow that exists downstream to an obstruction can be accomplished by threading the cannula tip 84 passed the blockage, or by entering the vessel through the skin downstream of the blockage.

Impedance measurements may be made during standard percutaneous imaging of vessels such as arteriography, venography, and cholangiography.

The device can also be used to measure the effectiveness of intravascular thrombolytic therapy. The cannula 78 is left in the vessel, upstream of the obstruction, as is the current accepted clinical method. Thrombolytic agent is infused through the injection port 84. Periodically, the invention can be used to quickly determine the actual vessel impedance, thereby allowing for close monitoring of the thrombolytic therapy. Current methods require visits to the angiography suite and imaging of the vessel, in order to assess the progress of the therapy. Similarly, the invention can be used to measure a change in vessel impedance during laser, or mechanical atherectomy.

Any impedance data that are produced by the invention are stored in the control unit 14 and also are printed out in hard copy by the printer 16. The invention also includes an integral communications module 19 for the transmission of impedance data to remote locations using standard data communication methods. The impedance data could be transmitted to locations remote to the procedure, for analyses in real time. These data could also be transmitted to a central collection data bank for archival and research purposes Obviously many modifications and variations of the present invention are possible in light of the above teachings. It is therefore to be understood that within the scope of the appended claims the invention may be practiced otherwise than as specifically described.

I claim:

1. A device for measuring the impedance characteristics of a vessel in a living body, said device comprising:
an automatic injection means for injecting fluid into a vessel, flow of said fluid directly generating a change in luminal pressure in said vessel;
a pressure sensor means for measuring luminal pressure of said vessel;
a feedback control means, operably coupled to said automatic injection means and said pressure sensor means, for controlling fluid injection by said automatic injection means so as to maintain luminal pressure of said vessel at a selected value; and,
a means for determining the flow per unit time injected by said automatic injection means, whereby the flow rate necessary to maintain luminal pressure at the selected value can be determined.

2. The device of claim 1, further comprising a means for isolating said vessel from naturally occurring physiological flow, so that luminal pressure in said vessel is generated exclusively by the injection of fluid by said automatic injection means.

3. The device of claim 2, further comprising:
a means for automatically sequencing the feedback control means to generate at least two selected values of luminal pressure in said vessel, thereby automatically determining the flow rate necessary to maintain each of said selected values of luminal pressure.

4. The device of claim 3, further comprising:
a second pressure sensor means for measuring pressure in the vessel upstream from the point fluid is injected into the vessel by the automatic injection means, so that luminal pressure naturally occurring in the vessel can be determined.

5. The device of claim 4, further comprising:
a means, operably coupled to such second pressure sensor means and said automatic sequencing means, for automatically selecting the at least two values of luminal pressure within the range of naturally occurring luminal pressures detected by said second pressure sensor means.

6. The device of claim 4, wherein an operator can select the at least two luminal pressure value.

7. The device of claim 1, wherein said feedback control means causes said automatic injection means to cease injection after a preselected luminal pressure has been maintained in the vessel for a set period; and, wherein said device further comprises a means associated with said pressure sensor for monitoring luminal pressure decay occurring immediately after cessation of injection, thereby producing pressure-time decay data which can be used to calculate capacitance of the vessel.

8. A device for measuring the capacitive characteristics of a vessel in a living body, said device comprising:
an automatic injection means for injecting fluid into a vessel, flow of said fluid directly generating a change in luminal pressure in said vessel;
a pressure sensor means for measuring luminal pressure of said vessel;
a control means, operably coupled to said automatic injection means and said pressure sensor means, for controlling the rate of fluid injected by said automatic injection means so as to charge the vessel with a selected lumen pressure, followed by a cessation of injection flow, and
a means associated with said pressure sensor means for monitoring luminal pressure decay occurring immediately after cessation of injection flow, thereby producing pressure-time decay data which can be used to calculate capacitance of the vessel.

9. The device of claim 8, further comprising a means for isolating said vessel from naturally occurring physiological flow, so that luminal pressure in said vessel is generated exclusively by the injection of fluid by said automatic injection means.

10. The device of claim 9, further comprising:
a means for automatically sequencing the control means to at least two selected values of charging luminal pressure, with pressure decay measurements taken for each selected value, so that vessel capacitance can be measured over a range of luminal pressures.

11. The claim of claim 10, further comprising a second pressure sensor means for measuring pressure in the vessel upstream from the point fluid is injected into the vessel by the automatic injection means, so that luminal pressure naturally occurring in the vessel can be measured; and a means operably coupled to said second pressure sensor means and said automatic sequencing means, for automatically selecting the at least two values of luminal pressure within the range of naturally occurring luminal pressures detected by said second pressure sensor means.

12. The device of claim 10, wherein an operator can select the at least two luminal pressure values.

13. The device of claim 9, wherein said control means maintains luminal pressure at a selected value for a set time period, prior to the cessation of fluid injection, and, wherein said device further includes a means for monitoring the flow per unit time injected by said automatic injection means that is necessary to maintain said selected luminal pressure.

14. A device for measuring the dynamic impedance characteristics of a vessel in a living body, said device comprising:
an automatic injection means for injecting fluid into said vessel in a pulsatile manner, flow of said fluid directly generating a change in luminal pressure in said vessel;
a pressure sensor means for measuring luminal pressure of the vessel during and between each pulsatile injection;
a control means for causing said automatic injection means to inject a pulsatile fluid flow to generate a luminal pressure-time profile generally matching a target fluid pressure-time profile; and,
a means for determining the instantaneous injected flow rate occurring during each pulsatile injection.

15. The device of claim 14, further comprising a means for isolating said vessel from naturally occurring physiological flow, so that luminal pressure in said vessel is generated exclusively by the injection of fluid by said automatic injection means.

16. The device of claim 15, where in said control means uses luminal pressure detected by said pressure sensor means as feedback control and includes a means for successively altering the injected pulsatile flow profile until the resulting pressure-time profile in the vessel lumen matches the target pressure-time profile.

17. The device of claim 15, wherein said control means further includes a means for measuring the pressure-time profile in the vessel at a point removed from the point fluid is injected by said automatic injection means, and wherein said target pressure-time profile is said measured pressure-time profile.

18. The device of claim 15, wherein said control means further includes a means for measuring the pressure-time profile in a second vessel, and wherein the target pressure-time profile is the said measured pressure-time profile.

19. A device for controlling the injection of an imaging fluid into a vessel, said device comprising:
   an automatic injection means for injecting an imaging fluid into the vessel for imaging the vessel, flow of said imaging fluid directly generating a change in luminal pressure in said vessel;
   a pressure sensor means for measuring luminal pressure of said vessel; and
   a feedback control means, operably coupled to said automatic injection means and said pressure sensor means, for controlling the rate of fluid injected into the vessel so as to achieve, but not exceed a preselected luminal pressure.

20. The device of claim 19, wherein said automatic injection means generates a pulsatile flow pattern generally matching a target pressure time profile, so as to allow for injection of the contrast material at the vessels naturally occurring flow velocities.

21. A device for controlling the injection of an imaging fluid into a vessel, said device comprising:
   an automatic injection means for injecting an imaging fluid into the vessel for imaging the vessel, flow of said imaging fluid directly generating a change in luminal pressure in said vessel;
   a pressure sensor means for measuring luminal pressure of said vessel;
   a feedback control means, operably coupled to said automatic injection means and said pressure sensor means, for controlling the rate of fluid injected into said vessel so as to achieve a preselected luminal pressure so that imaging fluid can be injected at a safe pressure; and,
   a means for determining the flow per unit time injected by said automatic injection means, whereby the flow rate necessary to maintain luminal pressure at the selected value can be determined and flow impedance can be calculated.

22. A device for controlling the injection of a lytic solution into a vessel, said solution intended for the purpose of dissolving an obstruction of said vessel, said device comprising:
   an automatic injection means for injecting the lytic solution into the vessel, flow of said lytic solution directly generating a change in luminal pressure in said vessel;
   a pressure sensor means for measuring luminal pressure of said vessel; and,
   a feedback control means, operably coupled to said automatic injection means and said pressure sensor means, for controlling the rate of fluid injected into the vessel so that luminal pressure can be maintained at a preset level, generally not to exceed the normal physiologic pressure experienced by said vessel.

23. The device of claim 22, further including a means for determining the flow per unit time injected by said automatic injection means, whereby the flow rate necessary to maintain luminal pressure at the preset level can be determined and flow impedance can be calculated.

* * * * *